United States Patent
Hagan et al.

(10) Patent No.: US 7,407,511 B2
(45) Date of Patent: Aug. 5, 2008

(54) METHODS AND MATERIALS FOR CONNECTIVE TISSUE REPAIR

(75) Inventors: Cary P. Hagan, Germantown, TN (US);
Rick P. Swaim, Cordova, TN (US);
Kelly W. Schlachter, Bartlett, TN (US);
James J. Chao, Dallas, TX (US);
Hungnan Lo, Shaker Heights, OH (US)

(73) Assignee: Wright Medical Technology Inc, Arlington, TN (US)

( * ) Notice: Subject to any disclaimer, the term of this patent is extended or adjusted under 35 U.S.C. 154(b) by 883 days.

(21) Appl. No.: 10/845,402

(22) Filed: May 13, 2004

(65) Prior Publication Data

US 2005/0255140 A1 Nov. 17, 2005

(51) Int. Cl.
A61F 2/08 (2006.01)

(52) U.S. Cl. ............... 623/13.14; 623/13.11; 623/13.12

(58) Field of Classification Search .............. 424/422; 623/11.11, 13.11, 13.12, 13.14, 13.17, 13.18
See application file for complete search history.

(56) References Cited

U.S. PATENT DOCUMENTS

| | | | |
|---|---|---|---|
| 4,597,766 A | 7/1986 | Hilal et al. | |
| 4,772,288 A | 9/1988 | Borner et al. | |
| 4,834,752 A * | 5/1989 | Van Kampen | 623/13.14 |
| 4,865,871 A * | 9/1989 | Livesey et al. | 435/1.3 |
| 5,024,830 A * | 6/1991 | Linner | 435/40.52 |
| 5,061,283 A | 10/1991 | Silvestrini | |
| 5,078,744 A | 1/1992 | Chvapil | |
| 5,258,014 A * | 11/1993 | Harada et al. | 606/228 |
| 5,258,040 A | 11/1993 | Bruchman et al. | |
| 5,336,616 A * | 8/1994 | Livesey et al. | 435/395 |
| 5,527,341 A | 6/1996 | Gogolewski et al. | |
| 5,575,819 A | 11/1996 | Amis | |
| 5,702,422 A * | 12/1997 | Stone | 606/232 |
| 5,723,008 A | 3/1998 | Gordon | |
| 5,800,544 A * | 9/1998 | Demopulos et al. | 623/13.13 |
| 5,855,619 A * | 1/1999 | Caplan et al. | 623/23.72 |
| 5,860,978 A * | 1/1999 | McDevitt et al. | 606/72 |
| 6,083,244 A | 7/2000 | Lubbers et al. | |
| 6,106,556 A | 8/2000 | Demopulos et al. | |
| 6,485,503 B2 * | 11/2002 | Jacobs et al. | 606/215 |
| 6,497,726 B1 | 12/2002 | Carter et al. | |
| 6,514,515 B1 | 2/2003 | Williams | |
| 6,524,317 B1 * | 2/2003 | Ritchart et al. | 606/72 |
| 6,533,821 B1 | 3/2003 | Lally | |
| 6,616,694 B1 | 9/2003 | Hart | |
| 6,638,312 B2 | 10/2003 | Plouhar et al. | |
| 2001/0051815 A1 | 12/2001 | Esplin | |
| 2002/0022861 A1* | 2/2002 | Jacobs et al. | 606/216 |
| 2002/0072806 A1 | 6/2002 | Buskirk et al. | |
| 2002/0077631 A1* | 6/2002 | Lubbers et al. | 606/72 |
| 2002/0103542 A1 | 8/2002 | Bilbo | |

(Continued)

FOREIGN PATENT DOCUMENTS

EP 278713 3/1991

(Continued)

*Primary Examiner*—Sharon E. Kennedy (57) ABSTRACT

This invention is generally directed to methods and materials for connective tissue repair. The invention is more specifically related to methods and materials for the repair of tendons and ligaments, especially in the hand. Methods and materials for rotator cuff repair are also disclosed. The use of extraoperatively obtained scaffolding matrices is promoted when reapproximating the connective tissue.

19 Claims, 9 Drawing Sheets

U.S. PATENT DOCUMENTS

| | | | |
|---|---|---|---|
| 2002/0119177 A1* | 8/2002 | Bowman et al. | 424/423 |
| 2002/0133229 A1 | 9/2002 | Laurencin et al. | |
| 2002/0161400 A1 | 10/2002 | Demopulos et al. | |
| 2002/0173558 A1 | 11/2002 | Williams et al. | |
| 2003/0023304 A1 | 1/2003 | Carter et al. | |
| 2003/0023316 A1 | 1/2003 | Brown et al. | |
| 2003/0088270 A1 | 5/2003 | Lubbers et al. | |
| 2003/0097179 A1 | 5/2003 | Carter et al. | |
| 2003/0181889 A1 | 9/2003 | Little | |
| 2003/0212456 A1 | 11/2003 | Lipchitz et al. | |
| 2004/0078077 A1 | 4/2004 | Binette et al. | |
| 2005/0043805 A1* | 2/2005 | Chudik | 623/19.14 |
| 2007/0162121 A1* | 7/2007 | Tarrant et al. | 623/13.12 |
| 2007/0198087 A1* | 8/2007 | Coleman et al. | 623/13.18 |

FOREIGN PATENT DOCUMENTS

| | | |
|---|---|---|
| FR | 2638349 | 4/1990 |
| FR | 2690073 | 10/1993 |
| FR | 2748652 | 11/1997 |
| FR | 2810877 | 1/2002 |
| GB | 2282328 | 4/1995 |
| WO | WO01/06933 A2 | 2/2001 |
| WO | WO01/06933 A3 | 2/2001 |
| WO | WO01/28457 A1 | 4/2001 |
| WO | WO01/67944 A2 | 9/2001 |
| WO | WO03/034895 A3 | 5/2003 |
| WO | WO03/092761 A1 | 11/2003 |
| WO | WO03/095609 | 11/2003 |

* cited by examiner

METHODS AND MATERIALS FOR CONNECTIVE TISSUE REPAIR

FIELD OF THE INVENTION

This invention is generally directed to methods and materials for connective tissue repair. The invention is more specifically related to methods and materials for the repair of tendons and ligaments.

BACKGROUND OF THE INVENTION

Connective tissue in a person may rupture or tear for various reasons, including trauma, and therefore need to be repaired. Numerous methods and materials for repairing soft tissue have been proposed. As used herein, "connective tissue", generally refers to tendon and ligament.

Today, the most common methods of repairing torn, severed or otherwise damaged tendons involve approximating the severed ends of the tendons and suturing one side of the tendon to the other thereby returning the tendon to its natural position. A popular suture technique is the so-called Kessler technique and modifications thereof. Some of the other techniques include the Becker, Savage, lateral trap, double loop locking suture, four-strand interlock and variations of the Halsted technique.

Other current methods of tendon repair place prosthetic material either within or around the tendon or employ mechanical fasteners to the ends of the fasteners to reinforce the suture/tendon interface to provide a stronger repair. See e.g. U.S. Pat. No. 5,800,544; U.S. Pat. No. 6,080,192; U.S. Pat. No. 6,106,556, all of which are incorporated by reference herein as are all patents and published patent applications cited herein. However, these methods often may add bulk to the tendon which can result in problems with tendons that are in closely packed areas such as the hand.

Adhesives have also been proposed for tendon repair. See e.g. US Pub 2002/0161400. Similarly, photochemical treatments have been proposed. See e.g. US Pub 2002/0187935.

Various methods of placing a sleeve around the ends of the ruptured tendon have been proposed for acting as a support for suture. See e.g. U.S. Pat. Nos. 4,469,101; 5,147,400; 5,749,895; 5,897,591; 6,206,931; WO96/07355.

Alternatively, a method of placing a sleeve around the ends of the ruptured tendon has been proposed in which the sleeve has teeth thereon for attaching itself to the ends of the tendons. See e.g. U.S. Pat. No. 6,485,503; US Pub 2003/0069602; WO01/89392.

Finally, a method in which a metal insert is inserted into the ruptured ends of the tendon has been proposed. See e.g. U.S. Pat. No. 5,723,008; US Pub 2002/0161400.

In the art of ligament repair, the focus has been on the knee and in particular, the anterior cruciate ligament (ACL) and the posterior cruciate ligament (PCL). See e.g. U.S. Pat. No. 6,616,694; U.S. Pat. No. 6,497,726; U.S. Pat. No. 5,078,744; U.S. Pat. No. 4,597,766; EP 278,713. Typically, that repair involved the complete replacement of the remaining connective tissue with a graft of either autologous tendon harvested from patellar ligament or some other graft material. The graft may have various forms of fixation at its ends, such as bone plugs, anchors, or eyelets for screws.

Finally, methods of rotator cuff and shoulder muscle repair have been proposed. See e.g. US Pub 2003/0212456; FR 2,810,877; FR 2,690,073; FR 2,638,349; FR 2,748,652.

However, none of these various proposals of connective tissue repair have found a wide following.

Accordingly, there is room for improvement within the art.

OBJECTS OF THE INVENTION

It is an object of the invention to provide a method and material for connective tissue repair.

It is a further object of the invention to provide a method and material for connective tissue repair using an extra-operatively obtained scaffolding matrix.

It is a further object of the invention to provide a method and material for connective tissue repair using an extra-operatively obtained scaffolding matrix and that does not add bulk to the repaired connective tissue, especially when the connective tissue is tendon.

It is a further object of the invention to provide a method and material for connective tissue repair using an extra-operatively obtained scaffolding matrix that is especially suitable for use in the hand.

These and other objects of the invention are achieved by a method for repairing a tendon, comprising the steps of: accessing an end of a first tendon; accessing an end of a second tendon; extra-operatively obtaining a scaffolding matrix; joining the ends of the first and second tendons using the scaffolding matrix.

These and other objects of the invention are achieved by a material for use in connective tissue repair, comprising: an extra-operatively obtained scaffolding matrix, the matrix having a height, width, and length; the length being substantially greater than the width and the height; and the height and width being dimensioned such that said matrix may be sewn inside a tendon.

These and other objects of the invention are achieved by a method of repairing a ligament, comprising the steps of: accessing a first bone portion; accessing a second bone portion; accessing a ligament that should attach the first and second bone portions, but has come detached from one of the first and second bone portions; providing an extra-operatively obtained scaffolding matrix having first and second ends; attaching one end of the scaffolding matrix to the bone portions from which the ligament has become detached; attaching the scaffolding matrix to the ligament.

These and other objects of the invention are achieved by a method of rotator cuff repair, comprising the steps of: accessing the proximal humerus; accessing the scapula; providing a scaffolding matrix having first and second ends and at least one bone block on an end thereof; attaching the end of the scaffolding matrix having the bone block to the proximal humerus; attaching the other end of the scaffolding matrix to the scapula.

DETAILED DESCRIPTION OF THE INVENTION

With reference to the above-mentioned drawings, an exemplary embodiment of methods and materials for connective tissue repair that meets and achieves the various objects set forth above will now be described.

Tendon Repair

Figure 1:
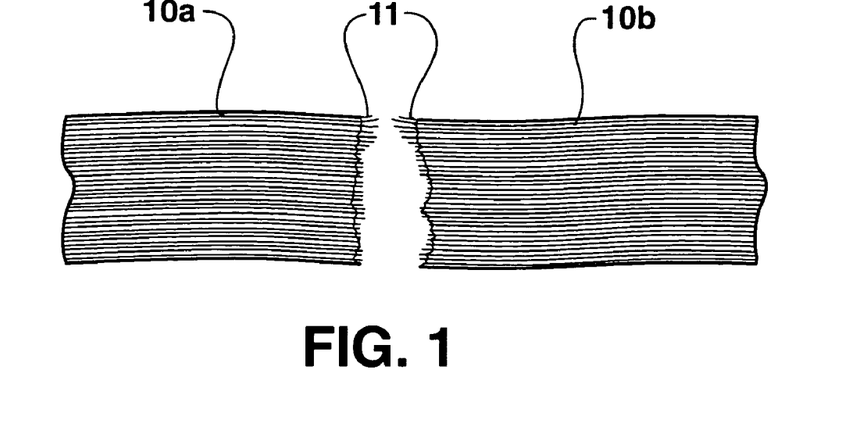
FIG. 1 depicts a severed or ruptured tendon for repair with the various aspects of the method according to the invention.

For example, in FIG. 1, a tendon 10 has been severed or ruptured into a first end portion 10a and a second end portion 10b of a tendon 10 and are in need of repair by re-connection of the two ends. These tendon end portions 10a, 10b may be located anywhere in the body and accessed via conventional surgical techniques. Tendons, such as tendon 10, are typically in the form of bundles of collagen fibers embedded in a connecting matrix, known as ground substance, provide the load carrying elements of natural tendons and ligaments. The arrangement of the collagen fibers is nearly parallel in tendons, equipping them to withstand high unidirectional loads. The less parallel arrangement of the collagen fibers in ligaments allows these structures to sustain predominant tensile stresses in one direction and smaller stresses in other directions. The ground substance in both tendons and ligaments acts generally as a cementing matrix holding the collagen fibers together. The ground substance retains large amounts of water essential to the non-compressive hydraulic function of the moving tissue. Also included in the tendon composition are elastic fibers, tenocytes, small blood vessels and nerves (none shown). In general, the cellular material (fibroblasts) occupies about 20% to 38% depending on references, of the total tissue volume, while the ground substance matrix accounts for the remaining 62% to 80%. About 70% of the ground substance matrix consists of water absorbed in an open polysaccharide matrix. Typically, when a tendon is severed, ruptured, or torn, the tendon ends will start to form frayed end portions 11 as the collagen fibers that make up tendon 10 start to separate from one another due to trauma and lack of blood.

In summary, according to preferred method of the invention, an extra-operatively obtained scaffolding matrix is used to connect the first and second end portions 10a, 10b. As used herein, and will be described in more detail below, "extra-operatively obtained", means not obtained by the surgical group currently performing the procedure or parties related to that group. Accordingly, extra-operatively is intended to exclude grafts obtained by such conventional procedures as autograft or allograft (where the graft is harvested at the same or near the same time as the surgery according to the invention—see below). Through the revascularization and repopulation of the scaffolding matrix the natural healing of the tendon 10 will be accelerated.

Furthermore, in summary, according to the invention, the scaffolding matrix is threaded through the first and second tendon end portions 10a, 10b, of the ruptured or severed tendon 10 and, if there is enough tendon available, then manipulated to bring the first and second tendon end portions into contact with each other (this is known as "re-approximation"). Additional suturing, using conventional suture, may then be carried out to further secure the ends of the tendon together.

The details of the method are set forth as follows.

Figure 2A:
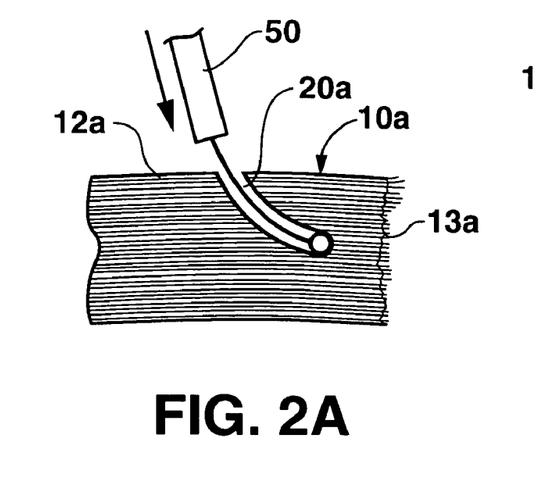
FIGS. 2A-C depict how a tunnel may be cored through the end of the ruptured or severed tendon for receipt of a scaffolding matrix according to the various aspects of the method according to the invention.
Figure 2B:
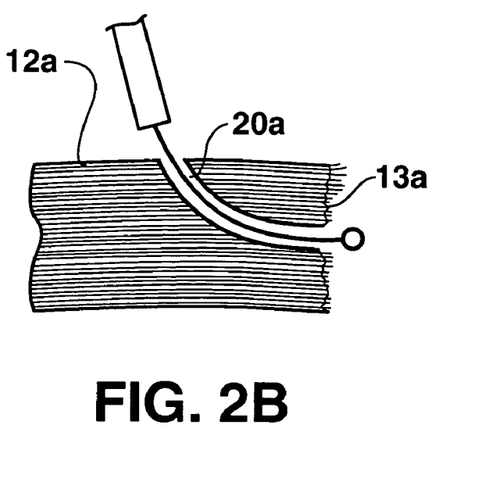
Figure 2C:
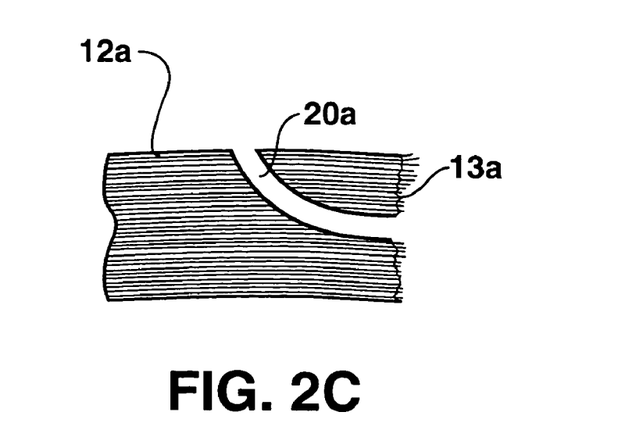

Step 1—As shown in FIGS. 2A-C, a ball probe 50 or tendon retriever 100 (FIG. 3) is used to core a tunnel 20a through the first tendon end portion 10a towards the severed or ruptured end 13a. An approach that enters the tendon end portion 10a through its lateral walls 12a and leads towards the severed or ruptured end 13a is preferred so as to not further fray the fibrous tendon. Further fraying of the end of the tendon is why it is believed that splint methods where the splints are inserted into the frayed ends of the tendon, such as shown in U.S. Pat. No. 5,723,003 and US Pub 2002/0161400, have not found a wide following.

Figure 3:
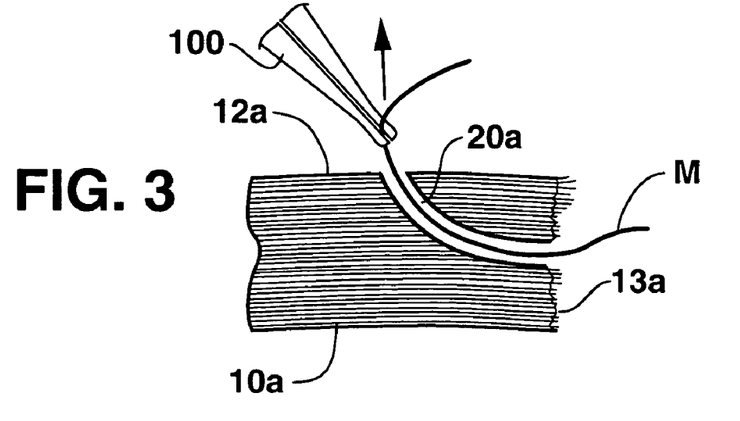
FIG. 3 depicts how the scaffolding matrix may be introduced and pulled through the tunnel cored through the ends of the ruptured or severed tendon according to the various aspects of the method according to the invention.

Step 2—A conventional tendon retriever 100 is used to grasp an end of the scaffolding matrix M and introduce it into and pull it back through the tunnel 20a in the end of the first tendon portion 10a (FIG. 3).

Figure 4:
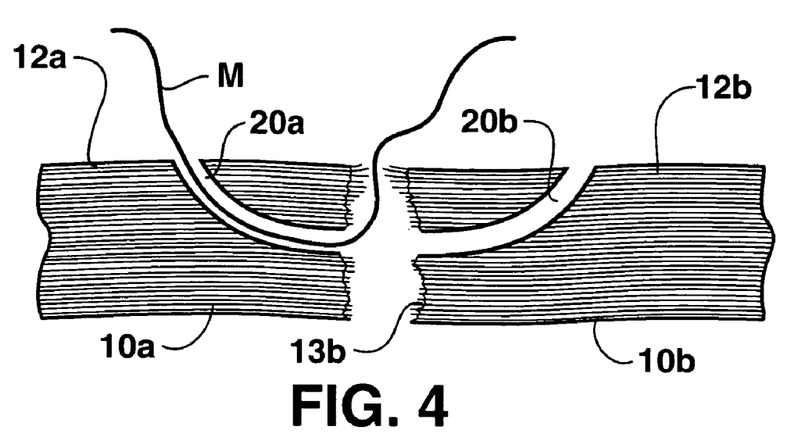
FIG. 4 depicts how a tunnel may be cored through the end of the other ruptured or severed tendon for receipt of a scaffolding matrix according to the various aspects of the method according to the invention.

Step 3—As with the first tendon end portion 10a, a ball probe or tendon retriever is used to core a tunnel 20b through the second tendon portion 10b towards the severed or ruptured end 13b. (FIG. 4).

Figure 5:
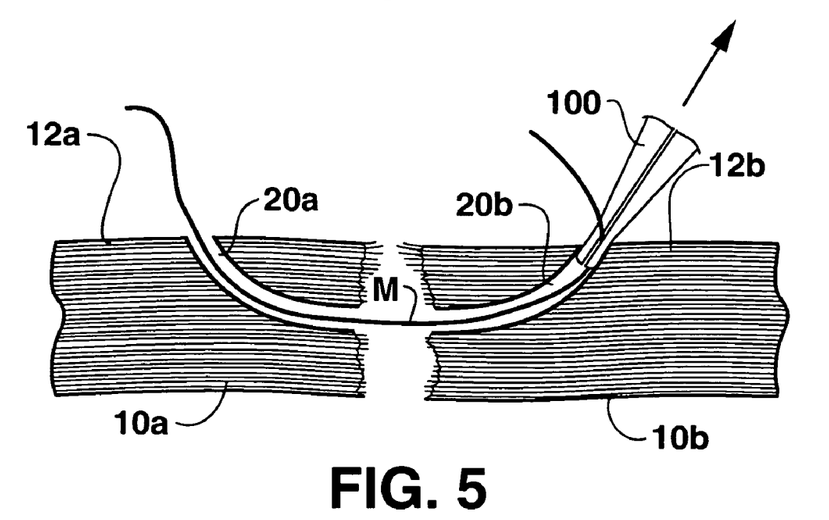
FIG. 5 depicts how the scaffolding matrix may be introduced and pulled through the tunnel cored through the end of the other ruptured or severed tendon according to the various aspects of the method according to the invention.

Step 4—A tendon retriever 100 is used to grasp the other end of the scaffolding matrix M and pull it back through the tunnel 20b in the end of the second tendon portion 10b. (FIG. 5).

Figure 6:
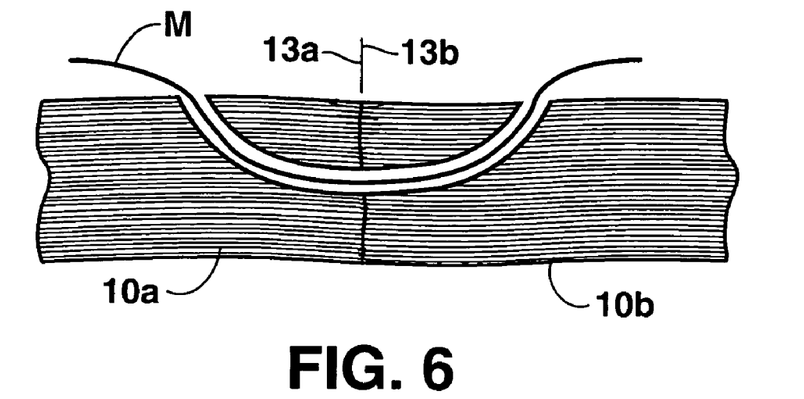
FIG. 6 depicts how the two ends of tendon are re-approximated and the scaffolding matrix pulled taught according to the various aspects of the method according to the invention.

Step 5—The ends of the two tendon portions 13a, 13b are re-approximated and the scaffolding matrix M is pulled taught. (FIG. 6).

Figure 7:
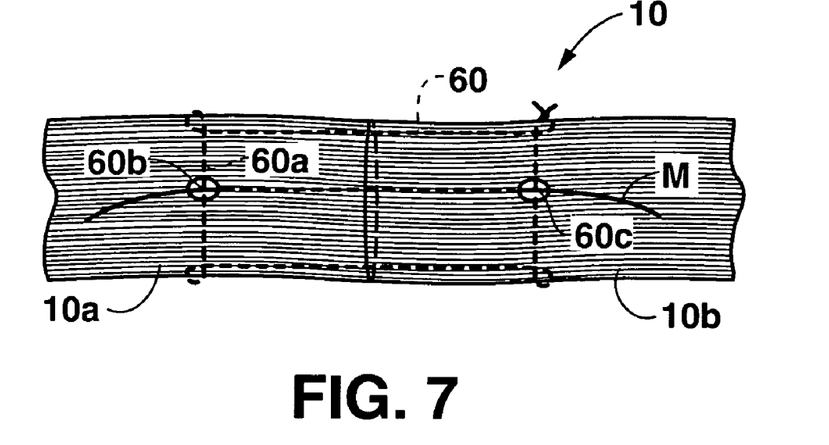
FIG. 7 depicts a first step in securing the scaffolding matrix to the ends of tendon according to the various aspects of the method according to the invention.

Step 6—Suture 60 is used to anchor the scaffolding matrix M and temporarily hold the end portions 10a, 10b of tendon 10 together while the scaffolding matrix M assists and accelerates the natural healing of the tendon 10. Kessler's suture method has been found to work well with the method of the invention. However, the invention is not limited to use of the Kessler method, as will be described. Typically, the first transverse stitch 60a of the Kessler pattern should be passed through and penetrate the scaffolding matrix M, such as at point 60b (FIG. 7). Conventional suture, such as 4.0 Ethibond® suture may be used for this purpose. The suture repair is made in a similar manner on both sides of the tendon tear (e.g. suture 60 passes through and penetrates scaffolding matrix M at point 60c).

Figure 8:
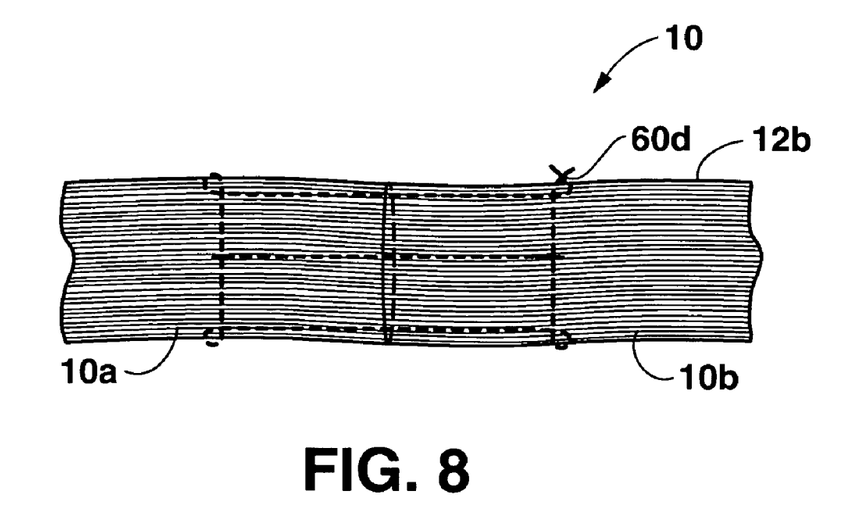
FIG. 8 depicts a second step in securing the scaffolding matrix to the ends of tendon according to the various aspects of the method according to the invention.

Step 7—The final knot 60d in the suture 60 is buried in the epitedineum of the tendon under lateral wall 11b and the scaffolding matrix M is cut flush with the tendon 10 by cutting off the excess portions of the scaffolding matrix M before and after 60a, 60b, respectively (FIG. 8).

Figure 9:
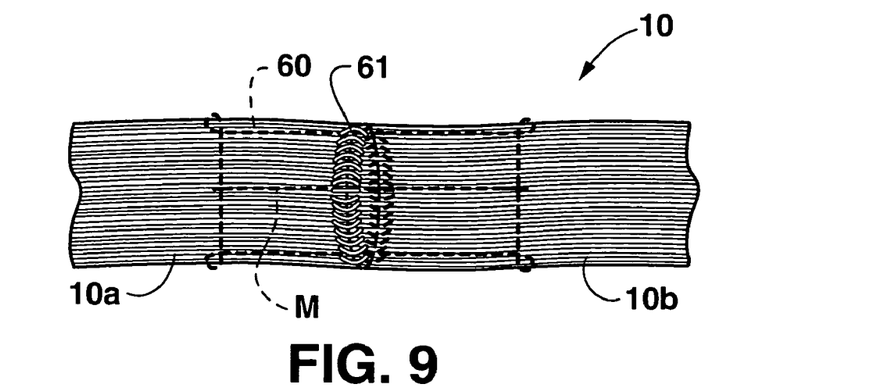
FIG. 9 depicts a third step in securing the scaffolding matrix to the ends of tendon according to the various aspects of the method according to the invention.

Step 8—A final stitch is made circumferentially around the tendon tear. Conventional suture 61, such as 6.0 BV Monofilament may be used for this purpose (FIG. 9).

According to the preferred method of the invention, the scaffolding matrix has been in the form of Graftjacket® cellular matrix, sold by Wright Medical Technology, Inc., of Arlington, Tenn., and manufactured according to U.S. Pat. Nos. 4,865,871; 5,024,830; and 5,336,616. This product consists of a selectively preserved extracellular protein matrix that is devoid of certain viable cells which normally express major histocompatibility complex antigenic determinants and other antigens which would be recognized as foreign by the recipient. This extracellular protein matrix is made up of collagen and other proteins and provides a structural template which may be repopulated with new viable cells that would not be rejected by the host. With this material complications following implantation (including but not limited to immunorejection, contracture, calcification, occlusion, and infection) are significantly reduced relative to current implant procedures and materials.

Preferably, the scaffolding matrix, when made from this particular material, should have a width of about 2 mm and a height of about 2 mm. Length is variable and depends upon the amount of stitching required. But, in general the material will be in strip form where the length is substantially greater than both the width and height.

In the past, doctors have been known to use fresh autograft and even allograft to make repairs similar to those described above. While it is not clear if such materials can be deemed "scaffolding matrices" because they are used more for their fixation properties than their repopulation properties, clearly, each of these pose their own problems. Autograft, while not prone to causing immune responses, is prone to causing complications and morbidity issues at the graft harvesting site and may not be possible in situations where poor tissue is found at typical harvest locations or the patient has other diseases that may result in poor harvesting ability. Allograft faces the primary hurdle of immune response issues in the recipient and therefore requires tissue matching between the donor and the recipient. Furthermore, typically the allograft is harvested from an identified donor on an as needed basis and if a proper donor or tissue type is not found at the time they are needed, the patient in the need of the graft will not be able to have one.

However, with a scaffolding matrix such as that described above (i.e., an acellular scaffolding matrix), not only are the harvesting complications and morbidity concerns of autograft non-issues, so are the immediacy and tissue matching concerns of allograft. Additionally, typically, acellular biological materials such as that described above have shelf lives of two years, thereby alleviating immediacy concerns. Furthermore, there is no need for anyone related to the tendon repair procedure to have any knowledge of the source of the scaffolding matrix, i.e., where or when it was harvested. In other words, the scaffolding matrix will be obtained extraoperatively and from an unknown source. Accordingly, as used herein, "unknown source" means unknown source with respect to the parties implanting the scaffolding matrix as a graft and not necessarily the parties harvesting the original material and then processing it according to, e.g., the various accelularization processes. The latter will, of course, rigorously monitor where the graft originates and certify its processing. Therefore, typically the scaffolding matrix will be an off-the-shelf material and not obtained as a step in the tendon repair process or in response to a request of the tendon repair process. Rather, the material will be sitting on the shelf waiting to be used and any package of material may be taken off the shelf with out the need to match with respect to the recipient's tissue type, etc.

As described, the method according to the invention has been discussed in the context of use with a performed form of an organic scaffolding matrix. However, various scaffolding matrices some of which have not yet been developed may be used. Accordingly, as used herein scaffolding matrix should be interpreted as any non-autograft or non-allograft (i.e., fresh) material capable of revascularization and repopulation by cells, especially connective tissue. Typically the material with be off-the-shelf material rather than harvested or produced as needed. It would also be beneficial if the material was strong. However, revascularization and the ability to be repopulated are more important to the fast healing of ruptured, severed, or torn tendons.

The scaffolding matrix need not even be from a human source. Graft materials from non-human sources, such as porcine, have been proposed. See e.g., U.S. Pat. No. 6,206,931.

Additionally, the scaffolding matrix need not even be organic. For example, synthetic porous materials capable of connective tissue in-growth may be used. See e.g. U.S. Pat. No. 5,258,040.

While the method according to the invention has been described as applicable to any tendon, the method is especially beneficial to the flexor tendons of the hand. This is due to the fact that the method involves placing the scaffolding matrix inside the tendon end portions and therefore does not add any bulk to the outside of the repaired tendons. Accordingly, the method should not inhibit the movement of the repaired tendons through the pulleys of the hand. As mentioned above, this is a problem with many prior art methods. See e.g. U.S. Pat. Nos. 5,800,544; 6,080,192; 6,106,556.

Figure 10A:
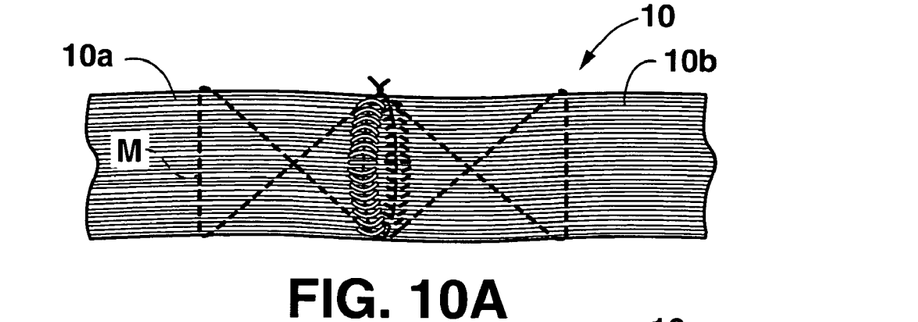
FIGS. 10A, 10B, and 10C depict alternative embodiments for stitching the scaffolding matrix according to the various aspects of the method according to the invention.
Figure 10B:
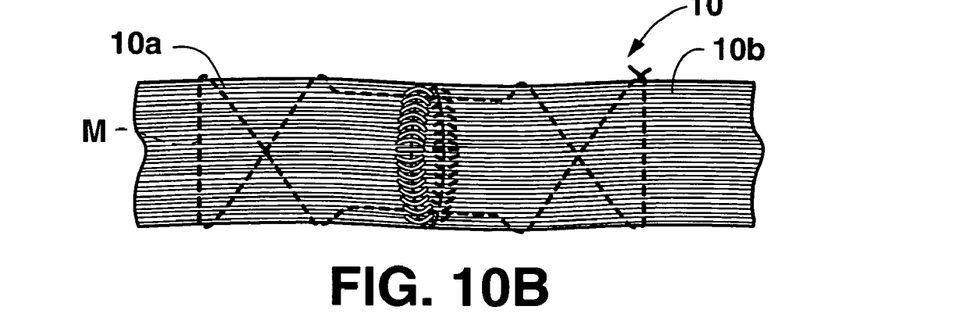
Figure 10C:
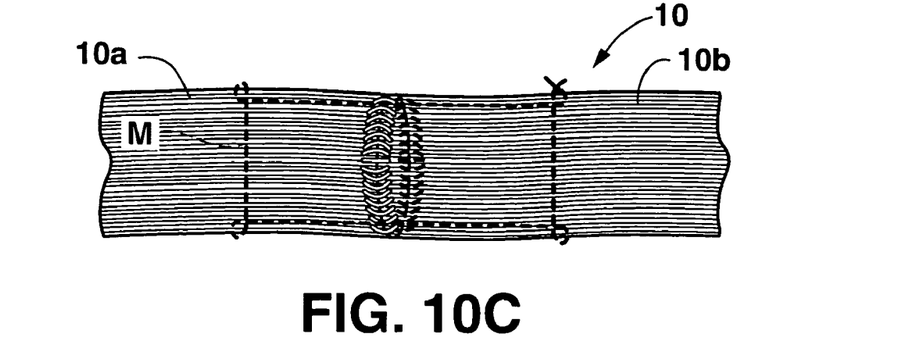

While the preferred form of the method according to the invention has been described above with respect to the use of suture to supplement and secure the scaffolding matrix to the ruptured ends of the tendon while the natural healing process takes place and is accelerated, that is not required. Indeed, doctors may choose to use the scaffolding matrix M in place of suture entirely. In such situations, doctors may treat the scaffolding matrix M as suture and use it with any known suturing method. For example, as shown in FIGS. 10A-C, the scaffolding matrix M may be used by itself with: Kienert's (FIG. 10A), Bunuell's (FIG. 10B), or Kessler's (FIG. 10C) methods. Additionally, as experience with these scaffolding matrices and stitching and manipulating them grows, specific new methods methods of stitching them may be developed.

Figure 11:
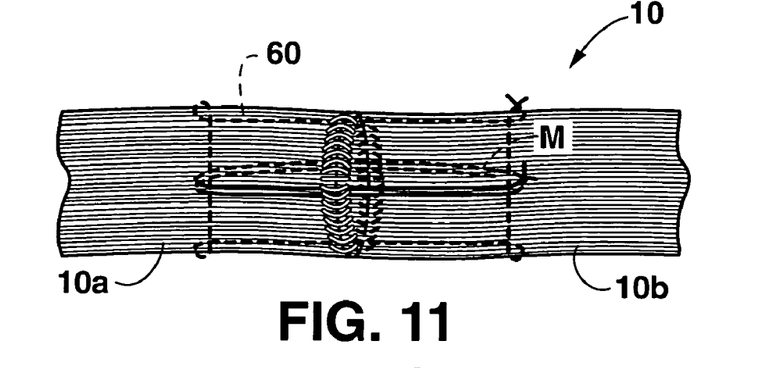
FIG. 11 depicts yet another alternative embodiment for stitching the scaffolding matrix according to the various aspects of the method according to the invention.

Furthermore, in yet other embodiments of the method according to the invention, it is possible to run the scaffolding matrix M two or more times back through the end portions 10a, 10b of the tendon 10 (FIG. 11).

Figure 12A:
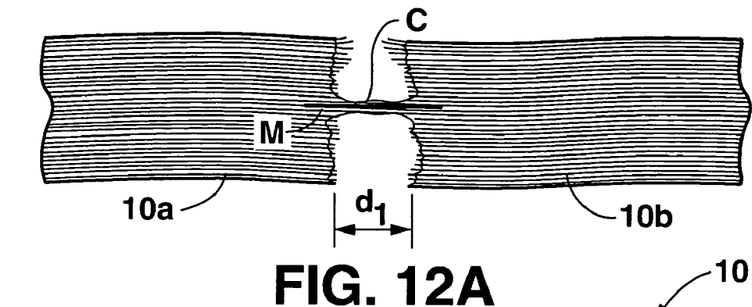
FIGS. 12A, 12B depict how the method according to the invention provides benefits over conventional methods with respect to tendon tears that cannot be re-approximated.
Figure 12B:
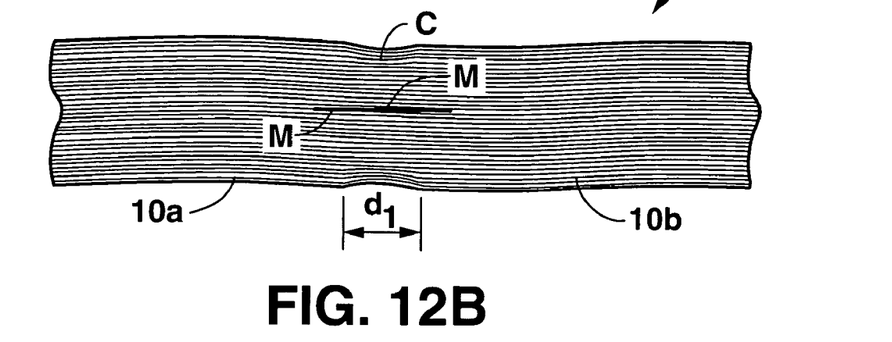
Figure 13:
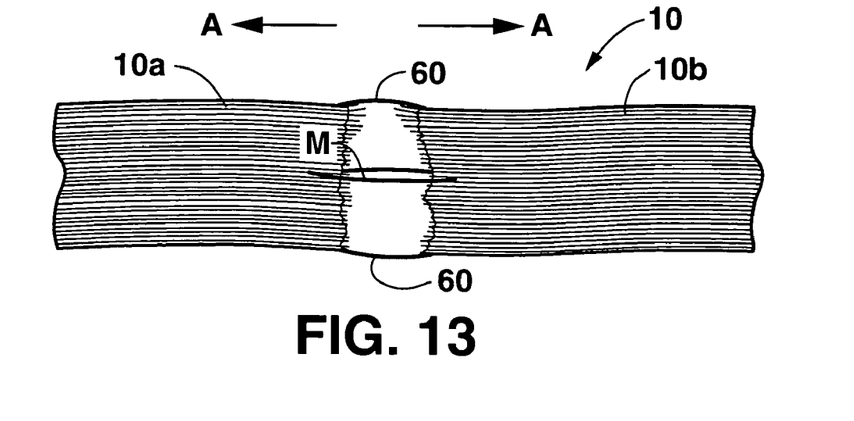
FIG. 13 depicts how the method according to the invention provides benefits over conventional suturing methods.

FIGS. 12A, 12B, and 13 depict additional benefits of the various aspects of the method according to the invention.

For example, FIGS. 12A and 12B depict how the method according to the invention provides benefits over conventional methods with respect to tendon tears that cannot be re-approximated. In such situations, due to either damaged tendon tissue that had to be excised or various other reasons, even the two end portions 10a, 10b of the tendon 10 are pulled to their natural tension; a gap d1 will exist between them (FIG. 12A). If this gap d1 is spanned by a material not capable of revascularization, repopulation and tissue ingrowth, such as suture, the two tendon end portions may be mechanically connected, but new connective tissue will never fill the gap d1 and the tendon will never repair to anywhere near its full strength or functionality. However, by use of the scaffolding matrix M, especially spanning from the inside of one tendon portion to the inside of the other tendon portion, new connective tissue C will begin to first repopulate the scaffolding matrix M (FIG. 12A) and then grow and build upon the scaffolding matrix M. This will lead, eventually, to the gap d1 being completely filled with new connective tissue C (FIG. 12B) and the tendon being repaired to a strength far in excess to that it would have otherwise achieved without the use of the scaffolding matrix M.

FIG. 13 depicts how the method according to the invention provides benefits over conventional suturing methods. In particular, it is known that suture connections may come loose if not fixated properly. In such cases, the two severed or ruptured end portions 10a, 10b of the tendon 10 may start to move apart, such as in the direction of arrows A. However, if a scaffolding matrix M capable of revascularization, repopulation and connective tissue ingrowth as discussed immediately above is used, even as a gap between the tendon end portions starts to form, natural healing can continue. Additionally, if the scaffolding matrix is one that provides for strength in excess to that of suture, the scaffolding matrix will act to keep the tendon end portions 10a, 10b together even as the suture may loosen.

Ligament Repair

In the art of ligament repair, as previously mentioned, the focus has been on the knee and in particular, the ACL and the PCL. See e.g. U.S. Pat. No. 6,497,726. Typically, that repair involved the complete replacement of the remaining connective tissue with a graft. The graft may have various forms of fixation at its ends, such as bone plugs, anchors, or eyelets for screws.

While such methods may be acceptable for larger joints such as the knee, simplified methods may be preferred in smaller joints, such as finger joints.

Figure 14:
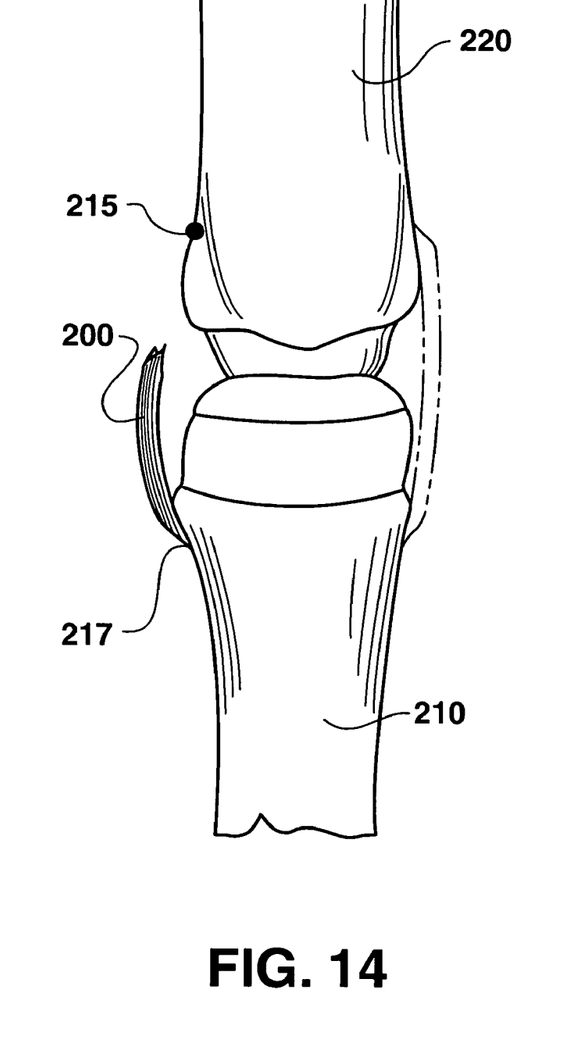
FIG. 14 depicts a separated finger ligament that may be repaired using the method according to the various aspects of the invention.

For example, FIG. 14, shows a separated finger ligament. In particular, in this example, the ligament 200 that would normally connect bones 210 and 220 has separated from its insertion point 215, while remaining connected to bone at its origin 217. Typically, after this occurs, as shown, the ligament 200 will begin to atrophy and shrink due to a lack of tension thereon.

According to the preferred method of the invention, after the bones 210 and 220 and ligament 200 are accessed via conventional surgical procedures, a piece of extra-operatively obtained scaffolding matrix M will be attached to the bone 220 at the original ligament 200 insertion point 215. The use of extra-operatively obtained scaffolding matrix M will provide for all the benefits described with respect to tendon repair above.

Figure 15:
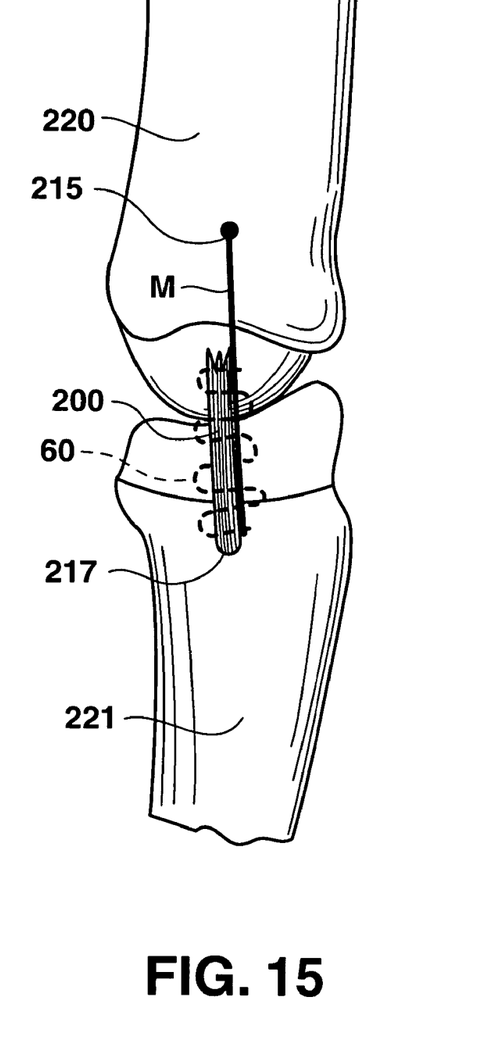
FIG. 15 depicts the ligament of FIG. 14 after being repaired using the method according to the various aspects of the invention.
Figure 16A:
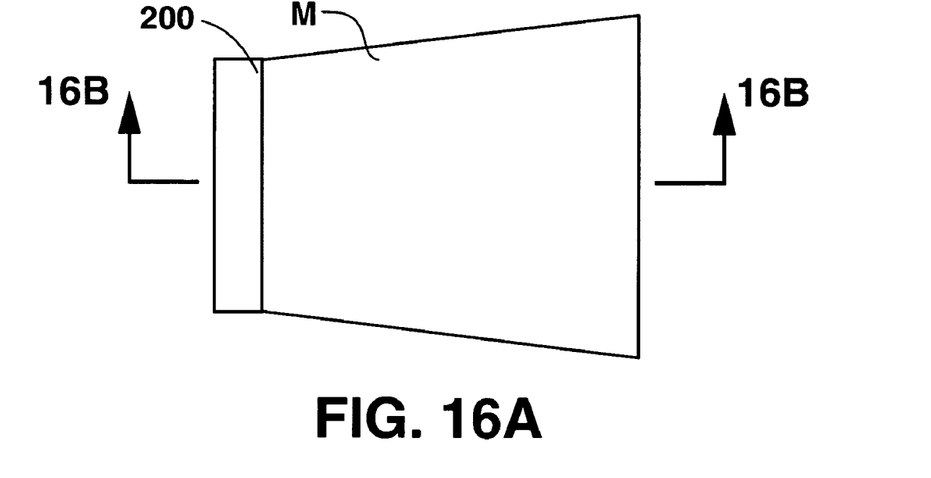
FIGS. 16A-16D depict various aspects of an exemplary embodiment of the invention suitable for use in rotator cuff repair.
Figure 16B:
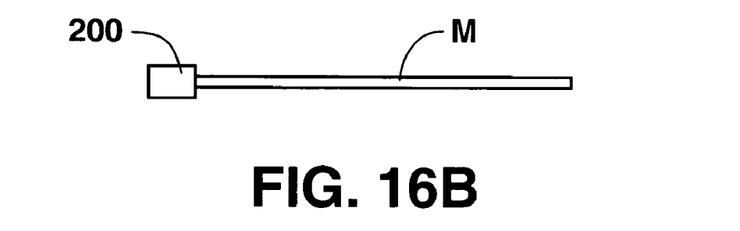
Figure 16C:
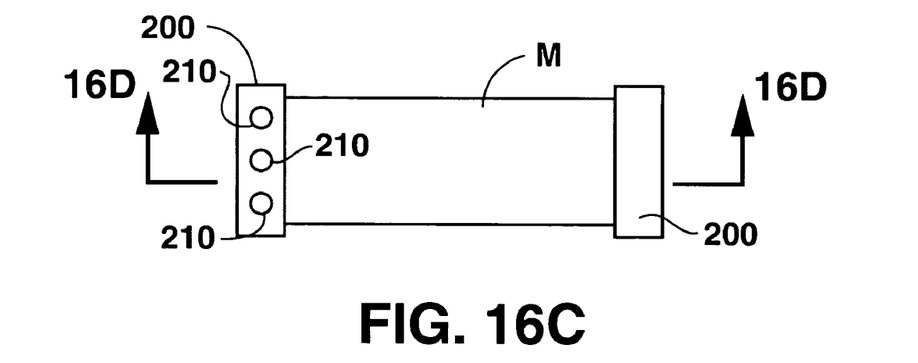
Figure 16D:
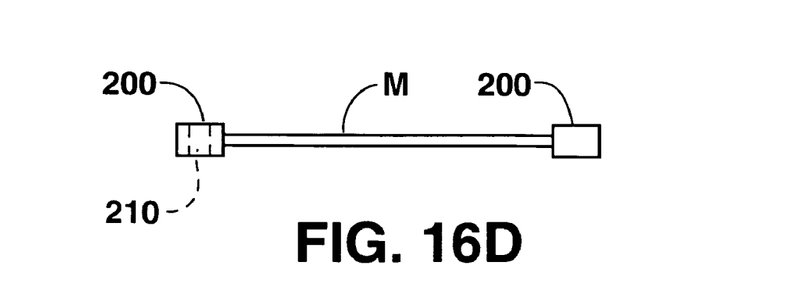

The scaffolding matrix M will be ran parallel to the existing ligament and attached thereto such as by suture 60, using any known method (FIG. 15). The ligament 200/scaffolding matrix M combination will now act as a complete natural ligament and give the finger back at least some of its natural movement. Furthermore, as the scaffolding matrix M becomes repopulated with connective tissue and begins to remodel itself to be more like connective tissue, the finger will begin to function even better.

When used for this application, scaffolding matrix M will typically be about 2 mm high by 3 mm wide. Again, length may vary depending upon the application and need.

While it has been suggested to use acellular graft materials to span bones, such has been done where movement between the bones has been wanted to be limited, see e.g. US Pub 2002/072806, and not promoted as is the case in joints such as fingers.

To further strengthen the repair, the doctor may chose to reinforce the ligament/scaffolding matrix combination by attaching it to both bones and not just the bone from which the ligament detatched (e.g. also attach to the origin 217 in FIG. 15 above).

The scaffolding matrix M according to the invention may have various forms of fixation at its ends, such as bone plugs, anchors, or eyelets for screws.

Rotator Cuff Repair

Scaffolding matrix M may be used for major tendon/ligament tears, such as in the rotator cuff of the shoulder. Materials useful for this purpose are shown in FIGS. 16A-16D. These materials comprise a sheet of scaffolding matrix M attached on one (FIGS. 16A, B) or both (FIGS. 16C, D) of its ends with a bone block. The bone block will be made from a bone material which has been thoroughly processed so as to eliminate tissue typing and pathogenic disease issues. Methods of producing such bone material and attaching it to materials similar to scaffolding matrix M are disclosed in, for example, U.S. Pat. Nos. 4,597,766; 6,497,726; US Pub 2002/0072806; US Pub 2003/0097179; WO01/06933. Additionally, one or both of the bone blocks may have screw holes 210 drilled therethrough to provide for additional fixation of the bone block to its fixation point.

Figure 17:
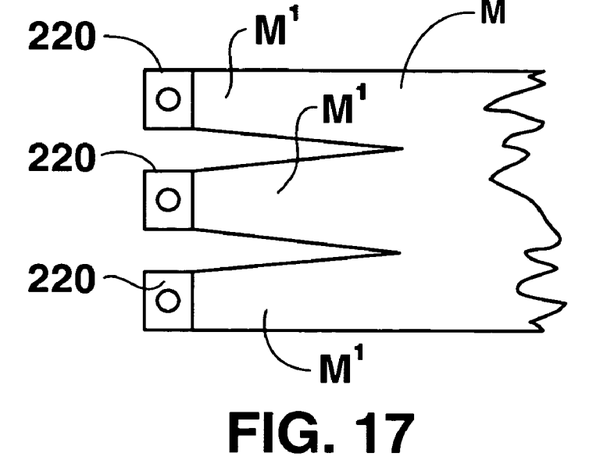
FIG. 17 depicts an exemplary embodiment of the invention suitable for use in rotator cuff repair through a closed arthroscopic approach.

FIG. 17 shows an embodiment especially suitable for use in arthroscopic rotator cuff repairs. In this embodiment, scaffolding matrix M has a main portion and then splits towards its end into a number of fingers M'. Each finger M' will have its own bone block 220, rather than one bone block span the entire width of scaffolding matrix M. This allows the entire scaffolding matrix/bone block construct to be rolled up and fed through an arthroscope canula.

Figure 18A:
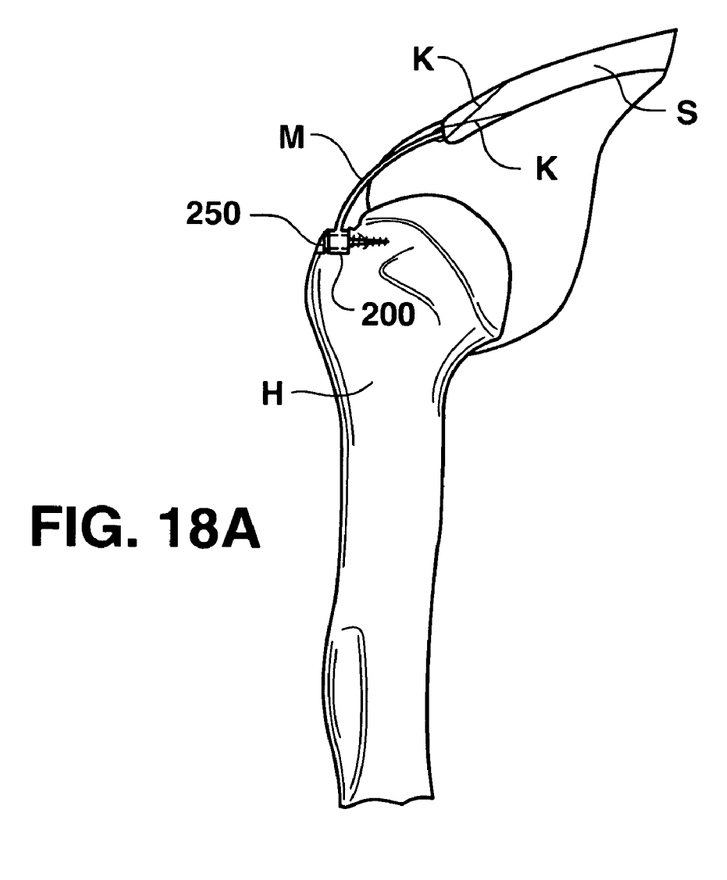
FIGS. 18A-18C depict various views of the embodiments of FIGS. 16A-16D being used to repair a rotator cuff.
Figure 18B:
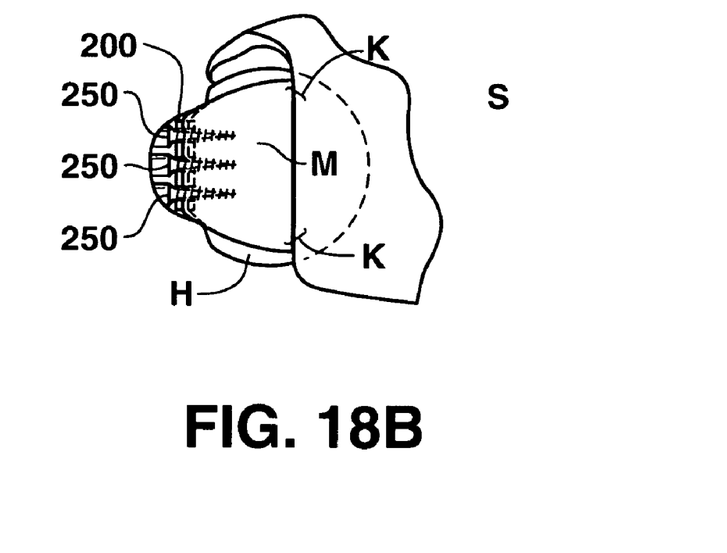
Figure 18C:
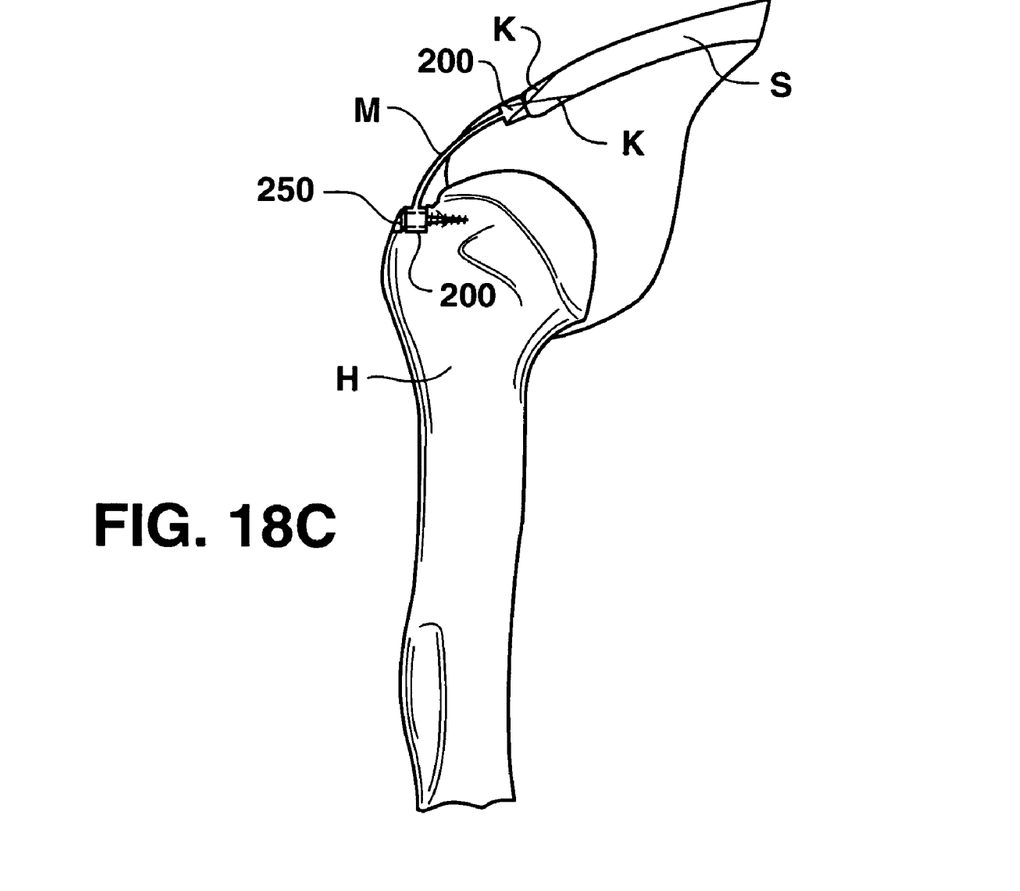

FIGS. 18A-C depict different ways in which these various embodiments may be used in rotator cuff repair. In FIG. a8A, bone block 200 is seated within a groove made in the proximal humerus H. A press-fit connection may be used that is supplemented by screws 250. Scaffolding matrix M spans humeral head and is fixed to the scapula S via k-wires K. In FIG. 18C, there is also a bone block on the proximal end of scaffolding matrix M and that bone block is also attached to scapula S by K-wires K.

To those skilled in the art to which this invention relates, many changes in construction and widely different embodiments and applications of the subject process and device will suggest themselves without departing from the spirit and scope of the invention. The disclosures and descriptions herein are purely illustrative and are not intended to be in any sense limiting.

That which is claimed:

1. A method of rotator cuff repair, comprising the steps of:
    accessing the proximal humerus;
    accessing the scapula;

providing a scaffolding matrix having first and second ends and at least one bone block on an end thereof;

attaching said end of said scaffolding matrix having said bone block to said proximal humerus;

attaching said other end of said scaffolding matrix to said scapula.

2. The method of claim 1, wherein said end of said scaffolding matrix having said at least one bone block has a plurality of separate bone blocks and said scaffolding matrix may be rolled up.

3. The method of claim 2, wherein said steps of accessing are carried out arthroscopically.

4. The method of claim 1, wherein said scaffolding matrix is configured as a sheet of scaffolding matrix.

5. The method of claim 4, wherein said sheet of scaffolding material has a rectangular configuration.

6. The method of claim 4, wherein said sheet of scaffolding material has a tapered configuration.

7. The method of claim 1, wherein said at least one bone block comprises a bone material which has been processed so as to eliminate tissue typing and pathogenic disease issues.

8. The method of claim 7, wherein said at least one bone block has screw holes formed therethrough for use in attaching said bone block in the rotator cuff repair.

9. The method of claim 2, wherein said scaffolding matrix has a main portion that splits into a plurality of fingers, each said finger having its own bone block consisting of one of said separate bone blocks.

10. The method of claim 1, further comprising making a groove in said proximal humerus, and seating said at least one bone block within said groove.

11. The method of claim 10, wherein said at least one bone block is seated in said groove in said proximal humerus via a press fit.

12. The method of claim 10, wherein said at least one bone block is secured in said groove in said proximal humerus via at least one screw.

13. The method of claim 1, wherein said scaffolding matrix spans a head of said proximal humerus and is attached to said scapula via k-wires.

14. The method of claim 1, further comprising a second bone block on said other end of said scaffolding matrix, and said second bone block attached to said scapula by K-wires.

15. The method of claim 1, wherein said scaffolding matrix comprises an extra-operatively obtained scaffolding matrix.

16. The method of claim 1, wherein said scaffolding matrix comprises a synthetic porous material.

17. The method of claim 1, wherein said scaffolding matrix comprises an organic scaffolding matrix.

18. The method of claim 17, wherein said scaffolding matrix comprises an acellular matrix.

19. The method of claim 18, wherein said scaffolding matrix does not produce an immune response upon implantation.

* * * * *